United States Patent [19]

Maldonado et al.

[11] 4,162,528
[45] Jul. 24, 1979

[54] X-RAY-FLUORESCENCE MEASUREMENT OF THIN FILM THICKNESSES

[75] Inventors: Juan R. Maldonado, Berkeley Heights; Dan Maydan, Short Hills, both of N.J.

[73] Assignee: Bell Telephone Laboratories, Incorporated, Murray Hill, N.J.

[21] Appl. No.: 892,105

[22] Filed: Mar. 31, 1978

Related U.S. Application Data

[63] Continuation-in-part of Ser. No. 863,466, Dec. 22, 1977, abandoned, which is a continuation of Ser. No. 687,462, May 18, 1976, abandoned.

[51] Int. Cl.² ..................... G06F 15/20; G01N 23/22
[52] U.S. Cl. .................................. 364/563; 250/273; 250/505; 364/571
[58] Field of Search ............... 364/563, 571; 250/273, 250/308, 272, 505, 277; 235/92 PC, 92 DN

[56] References Cited

U.S. PATENT DOCUMENTS

| | | | |
|---|---|---|---|
| 2,711,480 | 6/1955 | Friedman | 250/273 |
| 3,107,276 | 10/1963 | Cohen | 250/505 |
| 3,409,774 | 11/1968 | Dykeman | 250/273 |
| 3,984,679 | 10/1976 | Lublin et al. | 250/272 |
| 4,079,237 | 3/1978 | Schlesinger | 364/563 |
| 4,089,054 | 5/1978 | Ott | 364/563 |

OTHER PUBLICATIONS

Bertin; "Measurement of Thickness of Films and Platings"; Principles and Practice of X-ray Spectrometric Analysis; Plenum Press, N.Y. pp. 811-820; 1975.
Zimmerman; "Industrial Applications of X-ray Methods for Measuring Plating Thickness"; Advances in X-ray Analysis, vol. 4; Proc. of 9th Annual Conf. on Applications of X-ray Analysis held Aug. 10-12, 1960; Plenum Press, N.Y.; pp. 335-350; 1961.

*Primary Examiner*—Errol A. Krass
*Attorney, Agent, or Firm*—Lucian C. Canepa

[57] ABSTRACT

The thicknesses of the thin film components of a sample that comprises plural thin films deposited on top of each other on a substrate are simultaneously measured by an x-ray-fluorescence system. Incident x-rays excite x-ray fluorescence in the sample. Detection of the excited fluorescence is enhanced by a unique collimator assembly that is also adapted to enable direct monitoring of the intensity of the incident x-rays.

10 Claims, 2 Drawing Figures

X-RAY-FLUORESCENCE MEASUREMENT OF THIN FILM THICKNESSES

CROSS-REFERENCE TO RELATED APPLICATION

This application is a continuation-in-part of application Ser. No. 863,466, filed Dec. 22, 1977 and now abandoned, which is a continuation of application Ser. No. 687,462, filed May 18, 1976, also now abandoned.

BACKGROUND OF THE INVENTION

This invention relates to thickness measuring and, more particularly, to a method and an apparatus based on the phenomenon of x-ray fluorescence for simultaneously measuring the thicknesses of the thin film components of a sample that comprises plural thin films deposited on top of each other on a substrate.

The measurement of coating thickness by x-ray fluorescence is widely practiced in industry. Thus, for example, x-ray fluorescence is often employed to measure the coating thickness of a tin-coated steel member. Moreover, the technique has been suggested for use in determining the thicknesses of both platings of a nickel/copper-plated steel member.

For some time, workers in the plating art have been attempting to simultaneously measure small-area portions of multiply plated structures. Such measurements are, for example, of importance in the fabrication of various microelectronic devices in which, for reasons of economy, only very small areas are to be plated with multiple layers that include an expensive metal such as gold. The ability to perform these measurements in a high-accuracy and high-speed way is an important factor in being able to carry out such fabrication processes in an economically attractive manner.

SUMMARY OF THE INVENTION

Accordingly, an object of the present invention is a method and an apparatus based on the phenomenon of x-ray-fluorescence for simultaneously measuring the thicknesses of small areas of plural thin films deposited on a substrate.

Briefly, this and other objects of the present invention are realized in a specific illustrative embodiment thereof in which the thicknesses of nickel and gold films plated on a copper substrate are determined by measuring the intensity of various fluorescent lines excited in the metals in response to x-ray irradiation thereof. A detecting collimator, which is made of lead and has a conically shaped bore, includes a very small entrance aperture that is utilized to define the surface area of the top film from which excited fluorescence is to be detected. In addition, the collimator has an opening in the side thereof to allow some of the incident x-rays provided by the exciting source to enter the bore to excite fluorescence in the lead. This fluorescence is monitored by an associated detector as a measure of the intensity of the incident x-rays.

In accordance with the principles of the present invention, an x-ray-fluorescence system is initially calibrated in a systematic way to specify a set of parameters characteristic of the plated-metal configuration to be measured. Then a sample is irradiated by the system while the number of counts (photons excited by fluorescence) in each of selected characteristic lines of the platings and substrate is measured. The thicknesses of the plating layers are then calculated by an iterative procedure in accordance with specified relationships between the calibrated parameters and the measured counts.

BRIEF DESCRIPTION OF THE DRAWING

A complete understanding of the present invention and of the above and other objects and features thereof may be gained from consideration of the following detailed description presented hereinbelow in connection with the accompanying drawing in which.

DETAILED DESCRIPTION

Figure 1:
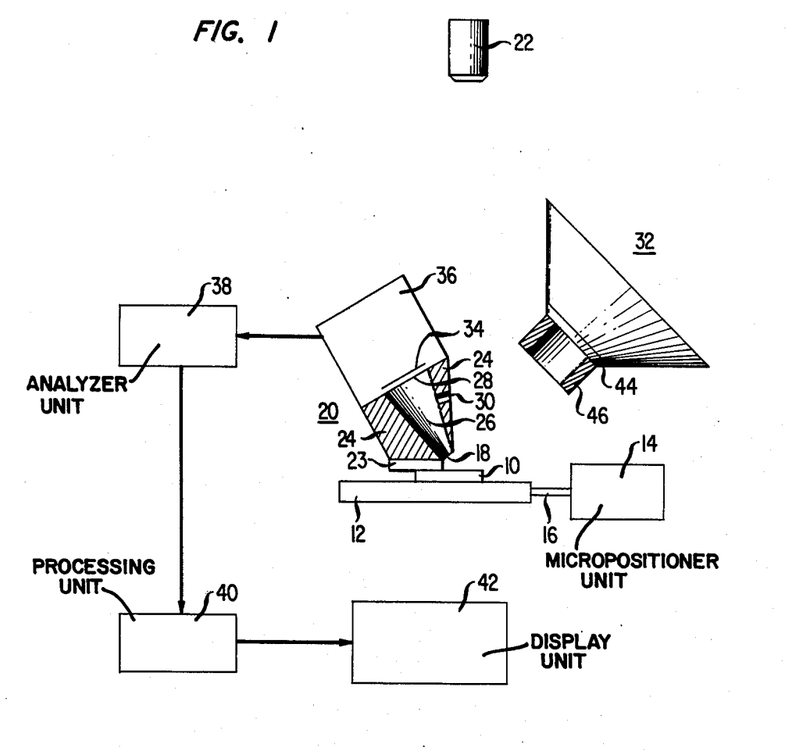
FIG. 1 is a schematic representation of a specific illustrative thickness measuring system made in accordance with the principles of the present invention.

The particular system shown in FIG. 1 is designed to simultaneously measure the thicknesses of plural thin films deposited on top of each other on a supporting substrate. By way of a specific example, emphasis herein will be directed initially to the case of measuring the thicknesses of two films that are deposited on a copper substrate whose thickness is at least 50 micrometers ($\mu$m). (For thinner copper substrates, the calibration procedure described below must be modified to include a copper substrate having the same thickness as that of the copper in the actual sample to be measured.) The sample to be measured will be assumed to include a 0.1-to-15-$\mu$m-thick film of nickel deposited directly on the top surface of the copper substrate. In turn, a 0.05-to-5-$\mu$m-thick film of gold is assumed to be deposited directly on the top surface of the nickel film. Such a trimetal system is of practical importance in the microelectronics field to form, for example, the tips of a conventional lead frame structure designed to achieve connections to an integrated circuit.

A trimetal sample 10 of the particular type specified above is shown in FIG. 1 mounted on a conventional x-y-z movable table 12. Precise movement of the table 12 is controlled by a standard x-y-z micropositioner unit 14 that is connected to the table via a mechanical coupler 16. By means of the unit 14, accurate positioning of the sample 10 with respect to the entrance aperture 18 of a detecting collimator 20 is achieved. Such positioning is facilitated by including in the depicted system a standard alignment telescope 22.

When finally positioned in place in the system of FIG. 1, a portion of the upper surface of the sample 10 is in intimate contact with a bottom planar surface of the collimator 20. Illustratively, this planar surface comprises the bottom of a glass plate member 23 which forms an integral part of the collimator structure.

In accordance with one aspect of the principles of the present invention, the collimator 20 of FIG. 1 includes a housing 24 made of lead having therein a truncated conical bore 26. Illustratively, the entrance aperture 18 of the bore 26 has a diameter of about 100 $\mu$m. The other or exit end 28 of the bore has a diameter of, for example, about 3.5 millimeters (mm). In one particular embodiment, the distance between the entrance and exit ends of the bore 26 was approximately 1 centimeter (cm).

In addition, the collimator 20 of FIG. 1 includes in the side thereof an aperture 30. This aperture is designed to propagate therethrough a portion of the radiation emitted by an x-ray source 32. In turn, the radiation transmitted through the aperture 30 impinges upon the lead wall of the bore 26 and is effective to excite x-ray-fluorescence (a PbL$_\beta$ line) in the lead housing. A portion of this excited fluorescence propagates toward the exit end 28 of the bore 26 and impinges upon a standard x-ray-detector 34 that is positioned in spaced-apart alignment with respect to the end 28. The number of counts of the PbL$_\beta$ line detected by the unit 34 constitutes a measure of the intensity of the radiation provided by the source 32. Accordingly, any variations in the x-ray-flux output of the source 32 will be detected by the depicted system. In response thereto suitable manual or automatic adjustments may be made to the source 32 to reestablish its output at a preselected level.

The small-entrance-aperture collimator 20 of FIG. 1 is effective to maximize the transmission of radiation emanating from a small surface area of the sample 10. In one particular illustrative embodiment of the present invention, the excited radiation collected in the bore 26 of the collimator 20 is that that emanates from an oval-shaped 100-μm by 140-μm surface area of the sample 10.

Another feature of the particular system shown in FIG. 1 is that by placing the sample 10 directly against a face of the detecting collimator unit 20, the unit 20 serves to establish the sample-to-detector distance of the system in a precise and fixed way and to thereby minimize measurement errors arising from variations in that distance.

The detector 34 shown in FIG. 1 comprises, for example, a standard lithium-doped silicon device contained in a nitrogen-cooled housing 36. In one particular illustrative embodiment, the detector 34 comprises a 3-mm-thick element having an effective diameter of about 4 mm. In that embodiment, the surface of the detector 34 that faces the collimator 20 is spaced about 3 mm away from the exit end 28 of the bore 26. An x-ray-transparent window made, for example, of beryllium is interposed between the end 28 and the detector 34.

The detector 34 of FIG. 1 responds to x-ray-fluorescence lines excited in the sample 10 to supply signals representative thereof to a standard multichannel x-ray analyzer unit 38. In the unit 38, respective counts of selected emitted lines are generated. Signals representative of these counts are then applied to a conventional processing unit 40 in which, as will be described in specific detail below, predetermined calibration data and calculation relationships are stored. In response to the measured line-count data applied thereto from the unit 38, the unit 40 calculates thickness values for the films included in the sample 10. For ease of presentation it is advantageous to apply these values to a unit 42 that comprises, for example, a standard visual display unit or a teletypewriter unit.

Illustratively, the x-ray source 32 shown in FIG. 1 includes a 10-μm-thick target dot of rhenium or tungsten about 3 mm in diameter deposited on a 250-μm-thick beryllium foil that is about 1.25 cm in diameter. In FIG. 1 this target-foil structure is designated by reference numeral 44. In a manner well known in the art, x-rays are produced by such a target in response to the impingement thereon of a high-energy beam of electrons.

X-rays prduced by the source 32 of FIG. 1 are directed toward the sample 10. To limit the lateral extent of this radiation, a lead cylinder 46 or other suitable beam-limiting element is included as an integral part of the source 32.

Figure 2:
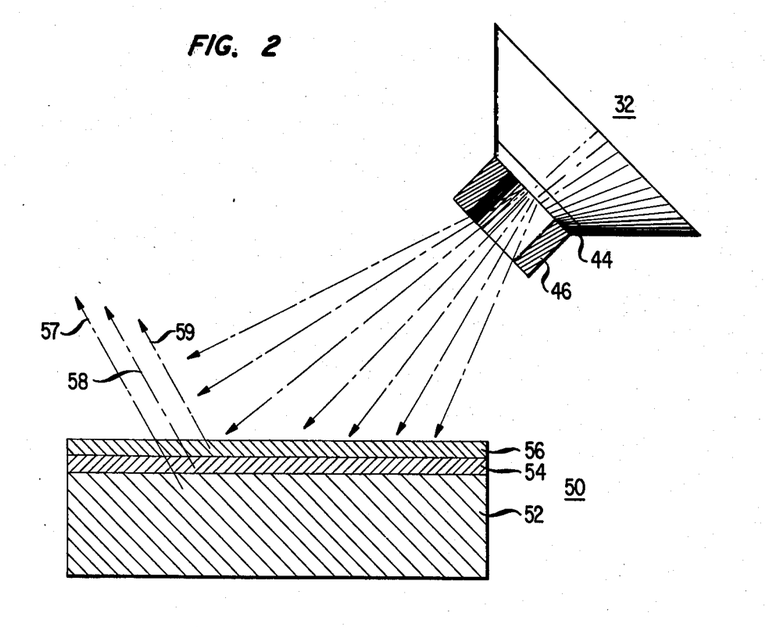
FIG. 2 shows a multi-layer sample being irradiated with x-rays to excite characteristic x-ray-fluorescence therein.

The irradiation by x-rays of a particular sample 50 to be measured is depicted in a simplified way in FIG. 2. X-rays emitted by the source 32 are directed at the top surface of the sample 50. By way of a specific illustrative example, the sample 50 is assumed to include a copper (Cu) substrate 52 having thereon thin layers 54 and 56 of nickel (Ni) and gold (Au), respectively. In accordance with one aspect of the principles of the present invention, the thicknesses of the gold and nickel layers of the depicted sample are determined by measuring the number of counts (photons excited by fluorescence) in selected characteristic lines of the metals 52, 54 and 56. In particular, the magnitude of the CuK$_\alpha$, NiK$_\alpha$ and AuL$_\alpha$ lines from the sample 50 are measured by the system shown in FIG. 1 as a basis for determining the thicknesses of the layers 54 and 56. In FIG. 2, dashed lines 57 through 59 schematically represent the radiation emitted by the excited sample in the CuK$_\alpha$, NiK$_\alpha$ and AuL$_\alpha$ line windows, respectively. As specified above in connection with the description of FIG. 1, only the radiation emitted from a small-area portion of the surface of the sample is collected by the collimator 20 and directed to the detector 34.

Before measuring selected lines emitted by an excited sample whose thin film thicknesses are to be determined, the arrangement of FIG. 1 must first be calibrated. By way of a specific example, a calibration procedure for a Au-Ni-Cu metal system will be set forth. But it should be realized that the procedure is in fact a general purpose one applicable to calibrating the FIG. 1 arrangement for measuring a variety of other trimetal systems. In each such other case one would, in the procedure specified below, simply replace the notation Au, Ni or Cu with the notation of the corresponding metal in another trimetal system. Thus, for example, if an indium layer is substituted for the nickel layer 54 of FIG. 2, the procedure below is modified by substituting the notation In for Ni wherever it appears.

The calibration and successful operation of a multilayer measuring system of the type described herein are based on particularizing various interactions that occur between layers during the measuring process. These interactions include the absorption by an upper layer of incident radiation that would be effective to excite fluorescence in a lower layer. Another effect is so-called secondary fluorescence which occurs when lines excited in one layer induce fluorescence in other layers thereby increasing the total fluorescence from the other layers. In addition, fluorescence emitted from a submerged layer is attenuated by its overlying layer(s) before emanating from the surface of the sample being measured.

In accordance with the principles of the present invention, a fixed-physical-geometry system of the type shown in FIG. 1 is initially calibrated by measuring the response of the system to a set of standard samples. Again, for illustrative purpose only, a particular Au-Ni-Cu metal system will be assumed. After the system is calibrated, there is placed in position therein an unknown Au-Ni-Cu sample. By measuring the number of counts in the AuL$_\alpha$, NiK$_\alpha$ and CuK$_\alpha$ line windows of the unknown sample in response to x-ray excitation, the calibrated system is able to automatically calculate values for the thicknesses of the Au and Ni layers.

A specific illustrative procedure to be followed to calibrate the FIG. 1 system, for thin films deposited on copper substrates thicker than 50 μm, is as follows:

A. Measure the number of counts in the CuK$_\alpha$ line window in response to x-ray excitation of an uncoated copper substrate having a thickness greater than 50 μm. This measured parameter is designated CuK$_{\alpha\infty}$. (The number of counts is a measure of the number of photons emitted from the excited substrate at the wavelength of the CuK$_\alpha$ line. The thickness of the substrate is directly but not linearly proportional to the measured count). During this step of the calibration procedure, the number of counts in the PbL$_\beta$ line window arising from excitation of the collimator 20 caused by x-rays entering the bore 26 via the opening 30 is also measured.

B. Measure the number of counts in the NiK$_\alpha$ line window in response to x-ray excitation of an uncoated nickel substrate having a thickness greater than 50 μm. This measured parameter is designated NiK$_{\alpha\infty}$.

C. Measure the number of counts in the AuL$_\alpha$ line window in response to x-ray excitation of an uncoated gold substrate having a thickness greater than 10 μm. This measured parameter is designated AuL$_{\alpha\infty}$.

d. For a standard sample comprising a layer of known-thickness gold (in the range 0.1 μm to 3 μm) on a greater-than-50-μm-thick copper substrate, measure the number of counts in the CuK$_\alpha$ line window in response to x-ray excitaton of the standard sample. A parameter designated $$\alpha_{CuK\alpha}^{Au}$$

is derived from the measured count and specifies the per-unit-thickness attenuation effect of gold both to the incident x-ray beam and to the excited CuK$_\alpha$ line.

E. For a standard sample comprising a layer of known-thickness gold (in the range 0.1 μm to 3 μm) on a greater-than-50-μm-thick nickel substrate, measure the number of counts in the NiK$_\alpha$ line window in response to x-ray excitation of the standard sample. A parameter designated $$\alpha_{NiK\alpha}^{Au}$$

or $\alpha_1$ is derived from the measured count and specifies the per-unit-thickness attenuation effect of gold both to the incident x-ray beam and to the excited NiK$_\alpha$ line.

F. For a standard sample comprising a layer of known-thickness nickel (in the range 0.1 μm to 2 μm) on a greater-than-50-μm-thick copper substrate, measure the number of counts in the CuK$_\alpha$ line window in response to x-ray excitation of the standard sample. A parameter designated $$\alpha_{CuK\alpha}^{Ni}$$

is derived from the measured count and specifies the per-unit-thickness attenuation effect of nickel both to the incident x-ray beam and to the excited CuK$_\alpha$ line.

G. For the same standard sample specified above in step F, a parameter $\alpha_3$ is determined from the relationship $$t_{NiK} = \frac{1}{\alpha_3} \ln\left(1 - \frac{NiK_\alpha}{NiK_{\alpha\infty}}\right)^{-1}$$

where $t_{NiK}$ is the known thickness of the nickel layer, NiK$_\alpha$ is the number of counts measured in the KiK$_\alpha$ line window in response to x-ray excitation of the sample and NiK$_{\alpha\infty}$ is the parameter specified above in step B.

H. For the same standard sample specified above in step B, a parameter $\alpha_5$ is determined by dividing the number of counts of the NiK$_\beta$ line measured in the Cuk$_\alpha$ line window by the number of counts measured in the NiK$_\alpha$ line window.

I. For a standard sample comprising a layer of known-thickness gold (in the range 0.1 μm to 3 μm) on a supporting substrate made of an x-ray-transparent material, a parameter $\alpha_6$ is determined from the relationship $$t_{AuK} = \frac{1}{\alpha_6} \ln\left(1 - \frac{AuL_\alpha}{AuL_{\alpha\infty}}\right)^{-1}$$

where $t_{AuK}$ is the known thickness of the gold layer, AuL$_\alpha$ is the number of counts measured in the AuL$_\alpha$ line window in response to x-ray excitation of the sample and AuL$_{\alpha\infty}$ is the parameter specified in step C above.

J. Several standard samples of different thicknesses are prepared. Each sample comprises layers of different known thicknesses of gold and nickel on a thick copper substrate. The known thicknesses are selected to fall in the range of thicknesses expected to be encountered in practice in making actual measurements on unknown samples. For each sample, the number of counts in the NiK$_\alpha$ and CuK$_\alpha$ line windows in response to x-ray excitation of the sample are measured. Then the thicknesses $t_{Ni}$ and $t_{Au}$ of the nickel and gold layers, respectively, of each sample are calculated in accordance with the following relationships:

$$t_{Ni} = \frac{1}{\alpha_3} \ln\left(1 - \frac{NiK_\alpha}{NiK_{\alpha\infty}} e^{\alpha_{NiK\alpha}^{Au} t_{AuK}}\right)^{-1}$$

$$t_{Au} = \frac{1}{\alpha_{CuK\alpha}^{Au}} \ln\left(\frac{CuK_{\alpha\infty} e^{-\alpha_{CuK\alpha}^{Ni} t_{NiK}}}{CuK_\alpha - \alpha_5 NiK_\alpha(1 + (\alpha_{NiK\alpha}^{Au} - \alpha_{CuK\alpha}^{Au}) t_{AuK})}\right)$$

where $t_{NiK}$ and $t_{AuK}$ are the known thicknesses of the nickel and gold layers, respectively, NiK$_\alpha$ and CuK$_\alpha$ are the respective measured counts in the NiK$_\alpha$ and CuK$_\alpha$ line windows and the parameters $\alpha_3$, $\alpha_5$, NiK$_{\alpha\infty}$, $$\alpha_{NiK\alpha}^{Au}, \alpha_{NiK\alpha}^{Au}, \alpha_{CuK\alpha}^{Au},$$

CuK$_\alpha$ and $$\alpha_{CuK\alpha}^{Ni}$$

are as defined in the steps specified above. Next, a parameter $\alpha_2$ is successively incremented in 0.01 steps and a corrected value for $\alpha_{NiK\alpha}^{Au}$ is calculated in accordance with the relationship $$\alpha_{cNiK\alpha}^{Au} = \alpha_1 - \alpha_2 t_{AuK}$$

for insertion in the relationships above for $t_{Ni}$ and $t_{Au}$ in place of $$\alpha_{NiK\alpha}^{Au}$$

until the calculated values of $t_{Ni}$ and $t_{Au}$ differ from the known thicknesses by less than a specified amount, the final value of $$\alpha_{cNiK\alpha}^{Au}$$

being designated $$\alpha_{CFNiK\alpha}^{Au}.$$

Obviously those steps in the calibration procedure set out above that are based on irradiation of the same standard sample (for example steps B and H) may be performed in consecutive sequence once the sample is mounted in place in the system of FIG. 1.

The various above-specified parameters determined during the calibration procedure are stored in the processor 40 of the FIG. 1 system. (Of course, the relationships specified in steps G, I and J above were also previously stored in the unit 40.) By utilizing those parameters and the measured line counts of the metals of an unknown-thickness trimetal sample, the actual thicknesses of the thin layers of the sample may be accurately determined.

Assume that a Au-Ni-Cu sample to be measured is positioned in place in the FIG. 1 system, which was previously calibrated as detailed above. The number of counts in each of the $AuL_\alpha$, $NiK_\alpha$ and $CuK_\alpha$ line windows of the sample in response to x-ray excitation is then measured. The initially assumed thickness $t_{AuF}$ of the gold layer of the sample is calculated by the FIG. 1 system in accordance with the following relationship (which was previously stored in the processor 40):

$$t_{AUF} = \frac{1}{\alpha_6} \ln\left(1 - \frac{AuL_\alpha}{AuL_{\alpha\infty}}\right)^{-1}$$

where $AuL_\alpha$ is the measured count in the $AuL_\alpha$ line window and $\alpha_6$ and $AuL_{\alpha\infty}$ were specified above during the calibration procedure. Next, the thickness $t_{Ni}$ of the nickel layer of the sample is calculated in accordance with the following relationship (which was specified above in step J of the calibration procedure):

$$t_{Ni} = \frac{1}{\alpha_3} \ln\left(1 - \frac{NiK_\alpha}{NiK_{\alpha\infty}} e^{\alpha_{CFNiK\alpha}^{Au} t_{AuF}}\right)^{-1}$$

where $NiK_\alpha$ is the measured count in the $NiK_\alpha$ line window and $\alpha_3$, $NiK_{\alpha\infty}$, $$\alpha_{CFNiK\alpha}^{Au}$$

and $t_{AuF}$ were specified above.

Subsequently, the thickness $t_{Au}$ of the gold layer of the sample is calculated in accordance with the following relationship (which was also specified above in step J of the calibration procedure).

$$t_{Au} = \frac{1}{\alpha_{CuK\alpha}^{Au}} \ln\left(\frac{CuK_{\alpha\infty} e^{-\alpha_{CuK\alpha}^{Ni} t_{Ni}}}{CuK_\alpha - \alpha_5 NiK_\alpha(1 + (\alpha_{CFNiK\alpha}^{Au} - \alpha_{CuK\alpha}^{Au}) t_{AuF})}\right)$$

where $CuK_\alpha$ is the measured count in the $CuK_\alpha$ line window and $$\alpha_{CuK\alpha}^{Au},$$

$CuK_{\alpha\infty}$, $$\alpha_{CuK\alpha}^{Ni},$$

$t_{Ni}$, $\alpha_5$, $NiK_\alpha$, $$\alpha_{CFNiK\alpha}^{Au}$$

and $t_{AuF}$ were specified above.

If the value for $t_{Au}$ calculated by the relationship immediately above differs from $t_{AuF}$ by more than a prescribed amount, the calculations for $t_{Ni}$ and $t_{Au}$ are successively iterated while using for $t_{AuF}$ each time the value just previously calculated for $t_{Au}$.

In the calculation procedure above, a value for $t_{AuF}$ can also be found, when the nickel thickness is less than 1 μm, by taking the ratio of the $AuL_\alpha$ count to the $CuK_\alpha$ count. For any thickness of nickel, the ratio of the $AuL_\alpha$ count to the $AuM_\alpha$ count also gives a value for $t_{AuF}$. In either case this value closely approximates $t_{Au}$. Accordingly, these ratios can be used as the bases for designing a simple system which measures the thickness of the gold layer only.

It is to be understood that the various above described techniques and arrangements are only illustrative of the application of the principles of the present invention. In accordance with these principles numerous modifications and variations may be devised by those skilled in the art without departing from the spirit and scope of the invention. For example, if thickness measurements are to be made of samples including elements whose atomic numbers are less than 13, the sample to be measured must be located in a vacuum chamber or in a helium atmosphere.

In addition, by manipulating several of the equations set forth earlier above to obtain therefrom specified ratios of measured line intensities to calibration line intensities, it is possible to obtain a system of two equations with two unknowns that are independent of geometrical variations in the measuring apparatus. For example, it is apparent from the expressions set forth earlier above that the fluorescence from the top gold layer of a trimetal gold-nickel-copper system is given by $$AuL_\alpha = AuL_{\alpha\infty}(1 - e^{-\alpha_6 t_{Au}}). \quad (1)$$

Similarly, it is apparent that the fluorescence from the nickel layer of such a system is given by $$NiK_\alpha = NiK_{\alpha\infty} e^{-\alpha_{Au}^{NiK_\alpha} t_{Au}} (1 - e^{-\alpha_3 t_{Ni}}). \quad (2)$$

Further, it is apparent that the $CuK_\alpha$ line from the substrate it attenuated by the nickel and gold layers and is given by $$CuK_\alpha = CuK_{\alpha\infty} e^{-\alpha_{Ni}^{CuK_\alpha} t_{Ni}} e^{-\alpha_{Au}^{CuK_\alpha} t_{Au}}. \quad (3)$$

From (1) and (3) above, we get (by division)

$$t_{Ni} = \frac{1}{\alpha_{Ni}^{CuK_\alpha}} \ln \frac{AuL_\alpha}{CuK_\alpha} \frac{CuK_{\alpha\infty}}{AuL_{\alpha\infty}} (1 - e^{-\alpha_6 t_{Au}}) e^{\alpha_{Au}^{CuK_\alpha} t_{Au}} \quad (4)$$

which may be expressed as $$t_{Ni} = f(\alpha_{Ni}^{CuK_\alpha}, AuL_\alpha, AuL_{\alpha\infty}, CuK_\alpha, \quad (5)$$
$$CuK_{\alpha\infty}, \alpha_6, \alpha_{Au}^{CuK_\alpha}, t_{Au}).$$

From (2) and (3) above, we get (by division)

$$t_{Au} = \frac{1}{\alpha_6 - \alpha_{Au}^{NiK_\alpha}} \ln \frac{NiK_\alpha}{CuK_\alpha} \frac{CuK_{\alpha\infty}}{NiK_{\alpha\infty}} \frac{e^{-\alpha_3 t_{Ni}}}{1 - e^{-\alpha_3 t_{Ni}}} \quad (6)$$

which may be expressed as $$t_{Au} = f(\alpha_6, \alpha_{Au}^{NiK_\alpha}, NiK_\alpha, NiK_{\alpha\infty}, CuK_\alpha, \quad (7)$$
$$CuK_{\alpha\infty}, \alpha_3, t_{Ni}).$$

By assuming a value of $t_{Au}$ calculated from (1) and using it in (4), we get a value for $t_{Ni}$. This value is used in (6) and a new value for $t_{Au}$ is thereby obtained. If this value of $t_{Au}$ differs by more than a prescribed amount from the initial value, the iteration is continued.

Expressions (1), (2), (3), (4) and (6) above may be written in a more general form for a trimetal system that comprises two thin films made of A and B deposited on top of each other on a substrate C. Expressions (1A), (2A), (3A), (4A) and (6A) below are the respective generalized counterparts of (1), (2), (3), (4) and (6) above.

$$AM = AM_\infty(1 - e^{-\alpha_6 t_A}) \quad (1A)$$

$$BM = BM_\infty(1 - e^{-\alpha_3 t_B}) e^{-\alpha_A^{BM} t_A} \quad (2A)$$

$$CM = CM_\infty e^{-\alpha_B^{CM} t_B} e^{-\alpha_A^{CM} t_A} \quad (3A)$$

$$t_B = \frac{1}{\alpha_B^{CM}} \ln \frac{AM}{CM} \frac{CM_\infty}{AM_\infty} (1 - e^{-\alpha_6 t_A}) e^{\alpha_A^{CM} t_A} \quad (4A)$$

$$t_A = \frac{1}{\alpha_6 - \alpha_A^{BM}} \ln \frac{BM}{CM} \frac{CM_\infty}{BM_\infty} \frac{e^{-\alpha_3 t_B}}{1 - e^{-\alpha_3 t_B}} \quad (6A)$$

Moreover, expressions (5) and (7) above may also be generalized. Expressions (5A) and (7A) below are the respective generalized counterparts of (5) and (7) above.

$$t_B = f(\text{Atten. } B/CM, AM, AM_\infty, CM, \quad (5A)$$
$$CM_\infty, \text{Atten. } A/CM, \alpha_F^B, t_A)$$

$$t_A = f(\text{Atten. } A/BM, BM, BM_\infty, CM, CM_\infty, \alpha_F^B, \alpha_F^A, t_B). \quad (7A)$$

The various terms included in the generalized expressions set forth above are defined as follows: Atten. B/CM is a measure of the per-unit-thickness attenuation effect of B in producing a specified line from C; Atten. A/CM is a measure of the per-unit-thickness attenuation effect of A in producing a specified line from C; Atten. A/BM is a measure of the per-unit-thickness attenuation effect of A in producing a specified line from B; Am is the measured magnitude of the count in a specified line window of the A layer; BM is the measured magnitude of the count in the specified line window of the B layer; CM is the measured magitude of the count in the specified line window of the C substrate; $AM_\infty$ is the measured magnitude of the count in the specified line window of the A substrate irradiated during the aforespecified calibration step; $BM_\infty$ is the measured magnitude of the count in the specified line window of the B substrate irradiated during the calibration step; $CM_\infty$ is the measured magnitude of the count in the specified line window of the C substrate irradiated during the calibration step; $\alpha_F^B$ is a parameter proportional to the intensity of fluorescent radiation emanating from metal B, $\alpha_F^A$ is a parameter proportional to the intensity of fluorescent radiation emanating from metal A; and $t_A$ and $t_B$ are, respectively, the thicknesses of the A and B layers.

We claim:

1. A method for simultaneously measuring in an x-ray-fluorescence system the thickness of two thin films made of A and B, respectively, deposited on top of each other on a substrate made of C, where A, B and C designate metals, said method comprising the steps of calibrating said measuring system by (A) irradiating with x-rays in said system known-thickness samples of an uncoated substrate of A, an uncoated substrate of B, an uncoated substrate of C, an uncoated layer of A, a layer of A on a substrate of C, a layer of A on a substrate of B, a layer of B on a substrate of C, and a layer of A on a layer of B on a substrate of C, (B) and measuring the number of counts in specified line windows of each of said uncoated samples to provide reference counts of the fluorescence excited therein and also measuring the number of counts in specified line windows of said coated samples to provide reference counts of the fluorescence excited therein including reference counts representative of the per-unit attenuation of the coating layers on fluorescence excited in the underlying layer or substrate, irradiating in said system an unknown-thickness A-on-B-on-C sample with x-rays to excite fluorescence in said unknown-thickness sample, measuring the respective number of counts in respective selected line windows of the metals A, B and C of said unknown-thickness sample in response to said irradiation, and calculating the thicknesses of the A and B constituents of said unknown-thickness sample in accordance with interaction formulae that relate the reference counts obtained during said calibration step with the counts obtained during measurement of the unknown-thickness sample.

2. A method as in claim 1 wherein said calculating step comprises (A) calculating an initially assumed thickness $t_{AF}$ of the A layer of said unknown-thickness sample in accordance with the following relationship:
$$t_{AF} = f(AM, AM_\infty)$$

where AM is the measured magnitude of the count in the specified line window of the A layer of said unknown-thickness sample and $AM_\infty$ is the measured magnitude of the count in the specified line window of the A substrate irradiated during the aforespecified calibration step, (B) calculating the thickness $t_B$ of the B layer of said unknown-thickness sample in accordance with the following relationship:
$$t_B = f(BM, BM_\infty, \text{Atten. } A/BM, t_{AF})$$

where BM is the measured magnitude of the count in the specified line window of the B layer of said unknown-thickness sample, $BM_\infty$ is the measured magnitude of the count in the specified line window of the B substrate irradiated during the aforespecified calibration step, and Atten. A/BM is a measure obtained during said calibration step of the per-unit-thickness attenuation effect of A in producing a specified line from B, (C) calculating the thickness $t_A$ of the A layer of said unknown-thickness sample in accordance with the following relationship:
$$t_A = f(\text{Atten. } A/CM, CM_\infty, \text{Atten. } B/CM, t_B, CM, BM, \text{Atten. } A/BM, t_{AF})$$

where Atten. A/CM is a measure obtained during said calibration step of the per-unit-thickness attenuation effect of A in producing a specified line from C, $CM_\infty$ is the measured magnitude of the count in the specified line window of the C substrate irradiated during the aforespecified calibration step, Atten. B/CM is a measure obtained during said calibration step of the per-unit-thickness attenuation effect of B in producing a specified line from C, and CM is the measured magnitude of the count in the specified line window of the C substrate of said unknown-thickness sample, (D) and, if $t_A$ calculated in step (C) differs from $t_{AF}$ by more than a prescribed amount, successively iterating steps (B) and (C) while using for $t_{AF}$ the value just previously calculated for $t_A$ in step (C).

3. A method as in claim 1 wherein said calculating step comprises specifying relationships (i), (ii) and (iii) respectively definitive of the fluorescence from A, B and C,
dividing (i) by (iii) to obtain a relationship (iv) definitive of the thickness $t_B$ of the B layer,
dividing (ii) by (iii) to obtain relationship (v) definitive of the thickness $t_A$ of the A layer,
calculating an initial value of $t_A$ from (i) and employing said initial value in (iv) to obtain a value for $t_B$,
calculating a value of $t_A$ from (v) and, if $t_A$ calculated from (v) differs from said initial value by more than a prescribed amount, successively iterating (iv) and (v) employing for $t_A$ in (iv) the value just calculated for $t_A$ in (v).

4. A method for simultaneously measuring the thicknesses of two thin films made of A and B, respectively, deposited on top of each other on a substrate made of C, where A, B and C designate metals, said method comprising the steps of irradiating in a measuring system an unknown-thickness A-B-C trimetal sample with x-rays to excite fluorescence in said sample, and simultaneously measuring the respective number of counts in respective selected line windows of the metals A, B and C of said sample in response to said irradiation, said method further including the steps of
calibrating said measuring system by irradiating with x-rays known-thickness samples of A alone, B alone, C alone, A on C, A on B, B on C and A on B on C to determine specified parameters of said system, and calculating the thicknesses of the A and B films in accordance with interaction formulae that relate said calibration parameters and said measured counts, wherein A, B and C are Au, Ni and Cu, respectively, and wherein said measuring step comprises measuring the number of counts in only the $AuL_\alpha$, $NiK_\alpha$ and $CuK_\alpha$ line windows in response to said irradiation.

5. In an x-ray-fluorescence system, a method for simultaneously measuring the thicknesses of small-area layers of a sample that comprises layers of metals A and B on a substrate made of metal C, said method comprising the steps of (A) calibrating said system to define the following parameters:

$CM_\infty$, which is the number of counts measured in a specified line window of C in response to x-ray excitation of an uncoated substrate made of C;

$BM_\infty$, which is the number of counts measured in a specified line window of B in response to x-ray excitation of an uncoated substrate made of B;

$AM_\infty$, which is the number of counts measured in a specified line window of A in response to x-ray excitation of an uncoated substrate made of A;

$a_{CM}{}^A$, which, for a layer of known-thickness A on a substrate made of C is a measure of the per-unit-thickness attenuation effect of A in producing a specified line from C in response to x-ray excitation;

$a_{BM}{}^A = a_1$, which, for a layer of known-thickness A on a substrate made of B is a measure of the per-unit-thickness attenuation effect of A in producing a specified line from B in response to x-ray excitation;

$a_{CM}{}^B$, which, for a layer of known-thickness B on a substrate made of C is a measure of the per-unit-thickness attenuation effect of B in producing a specified line from C in response to x-ray excitation;

$a_3$, which, for a layer of known-thickness B on a substrate made of C, is determined by the relationship:

$$t_{BK} = \frac{1}{\alpha_3} \ln\left(1 - \frac{BM}{BM_\infty}\right)^{-1}$$

where $t_{BK}$ is the known thickness of the B layer and BM is the number of counts measured in the specified line window in response to x-ray excitation;

$\alpha_5$, which, for an uncoated substrate made of B, is the number of counts of the specified line from B measured in a specified line window of C divided by the number of counts measured in the specified line window from B;

$\alpha_6$, which, for a layer of known-thickness A, is determined by the relationship:

$$t_{AK} = \frac{1}{\alpha_6} \ln\left(1 - \frac{AM}{AM_\infty}\right)^{-1}$$

where $t_{AK}$ is the known thickness of the A layer and AM is the number of counts measured in the specified line window from A in response to x-ray excitation;

$\alpha_2$, which, for layers of known thicknesses of A and B on a thick substrate made of C is determined by measuring the number of counts in the specified line windows from B and C in response to x-ray excitation; calculating $t_B$ and $t_A$ in accordance with the following relationships:

$$t_B = \frac{1}{\alpha_3} \ln\left(1 - \frac{BM}{BM_\infty} e^{\alpha^A_{BM} t_{AK}}\right)^{-1}$$

$$t_A = \frac{1}{\alpha^A_{CM}} \ln\left(\frac{CM_\infty e^{-\alpha^B_{CM} t_{BK}}}{CM - \alpha_5 BM(1 + (\alpha^A_{BM} - \alpha^A_{CM})t_{AK})}\right)$$

where $t_{BK}$ and $t_{AK}$ are the known thicknesses of the B and A layers, respectively, BM and CM are the respective measured counts in specified line windows from B and C in response to x-ray excitation; successively incrementing $\alpha_2$ in specified steps and calculating a corrected value for $\alpha^A_{BM}$ in accordance with the relationship $$\alpha_{C\,BM}{}^A = \alpha_1 - \alpha_2 t_{AK}$$

for insertion in said relationships above for $t_B$ and $t_A$ in place of $\alpha_{BM}{}^A$ until the calculated values of $t_B$ and $t_A$ differ from the respective known thicknesses by less than a specified amount, the final value of $\alpha_{C\,BM}{}^A$ being designated $\alpha_{CF\,BM}{}^A$;

(B) positioning a sample comprising said substrate with said layers thereon in said system for measurement;

(C) measuring the number of counts in specified line windows from A, B and C of said sample in response to x-ray excitation;

(D) calculating the initially assumed thickness $t_{AF}$ of the A layer of said sample in accordance with the following relationship:

$$t_{AF} = \frac{1}{\alpha_6} \ln\left(1 - \frac{AM}{AM_\infty}\right)^{-1}$$

where AM is the measured count in the specified line window from A;

(E) calculating the thickness $t_B$ of the B layer of said sample in accordance with the following relationship:

$$t_B = \frac{1}{\alpha_3} \ln\left(1 - \frac{BM}{BM_\infty} e^{\alpha CF^A_{BM} t_{AF}}\right)^{-1}$$

where BM is the measured count in the specified line window from B;

(F) calculating the thickness $t_A$ of the A layer of said sample in accordance with the following relationship:

$$t_A = \frac{1}{\alpha^A_{CM}} \ln\left(\frac{CM_\infty e^{-\alpha^B_{CM} t_B}}{CM - \alpha_5 BM(1 + (\alpha^A_{CFBM} - \alpha^A_{CM})t_{AF})}\right)$$

where CM is the measured count in the specified line window from C;

(G) and, if $t_A$ calculated in step (F) differs from $t_{AF}$ by more than a prescribed amount, successively iterating steps (E) and (F) while using for $t_{AF}$ the value just previously calculated for $t_A$ in step (F).

6. In an x-ray-fluorescence system, a method for simultaneously measuring the thicknesses of small-area layers of a sample that comprises layers of metals A and B on a substrate made of metal C, said method comprising the steps of (A) calibrating said system to define the following parameters:

$CK_{\alpha\infty}$, which is the number of counts measured in the $CK_\alpha$ line window in response to x-ray excitation of an uncoated substrate made of C;

$BK_{\alpha\infty}$, which is the number of counts measured in the $BK_\alpha$ line window in response to x-ray excitation of an uncoated thick substrate made of B;

$AL_{\alpha\infty}$, which is the number of counts measured in $AL_\alpha$ line window in response to x-ray excitation of an uncoated substrate made of A;

$\alpha_{CK_\alpha}{}^A$, which, for a layer of known-thickness A on a thick substrate made of C is a measure of the per-unit-thickness attenuation effect of A in producing a $CK_\alpha$ line in response to x-ray excitation;

$\alpha_{BK_\alpha}{}^A = \alpha_1$, which, for a layer of known-thickness A on a thick substrate made of B is a measure of the per-unit-thickness attenuation effect of A in producing a $BK_\alpha$ line in response to x-ray excitation;

$\alpha_{CK_\alpha}{}^B$, which, for a layer of known-thickness B on a thick substrate made of C is a measure of the per-unit-thickness attenuation effect of B in producing a $CK_\alpha$ line in response to x-ray excitation;

$\alpha_3$, which, for a layer of known-thickness B on a thick substrate made of C, is determined by the relationship:

$$t_{BK} = \frac{1}{\alpha_3} \ln\left(1 - \frac{BK_\alpha}{BK_{\alpha\infty}}\right)^{-1}$$

where $t_{BK}$ is the known thickness of the B layer and $BK_\alpha$ is the number of counts measured in the $BK_\alpha$ line window in response to x-ray excitation; p2 $\alpha_5$, which for an uncoated substrate made of B, is the number of counts of the $BK_\beta$ line measured in the $CK_\alpha$ line window divided by the number of counts measured in the $BK_\alpha$ line window;

$\alpha_6$, which, for a layer of known-thickness A, is determined by the relationship:

$$t_{AK} = \frac{1}{\alpha_6} \ln\left(1 - \frac{AL_\alpha}{AL_{\alpha\infty}}\right)^{-1}$$

where $t_{AK}$ is the known thickness of the A layer and $AL_\alpha$ is the number of counts measured in the $AL_\alpha$ line window in response to x-ray excitation;

$\alpha_2$, which, for layers of known thicknesses of A and B on a thick substrate made of C is determined by measuring the number of counts in the $BK_\alpha$ and $CK_\alpha$ line windows in response to x-ray excitation; calculating $t_B$ and $t_A$ in accordance with the following relationships:

$$t_B = \frac{1}{\alpha_3} \ln\left(1 - \frac{BK_\alpha}{BK_{\alpha\infty}} e^{\alpha^A_{BK_\alpha} t_{AK}}\right)^{-1}$$

$$t_A = \frac{1}{\alpha^A_{CK_\alpha}} \ln\left(\frac{CK_{\alpha\infty} e^{-\alpha^B_{CK_\alpha} t_{BK}}}{CK_\alpha - \alpha_5 BK_\alpha(1 + (\alpha^A_{BK_\alpha} - \alpha^A_{CK)\alpha}) t_{AK})}\right)$$

where $t_{BK}$ and $t_{AK}$ are the known thicknesses of the B and A layers, respectively, $BK_\alpha$ and $CK_\alpha$ are the respective measured counts in the $BK_\alpha$ and $CK_\alpha$ line windows in response to x-ray excitation; successively incrementing $\alpha_2$ in steps and calculating a corrected value for $\alpha_{BK_\alpha}{}^A$ in accordance with the relationship $$\alpha_{C\,BK_\alpha}{}^A = \alpha_1 - \alpha_2 t_{AK}$$

for insertion in said relationships above for $t_B$ and $t_A$ in place of $\alpha_{BK_\alpha}{}^A$ until the calculated values of $t_B$ and $t_A$ differ from the respective known thicknesses by less than a specified amount, the final value of $\alpha_{C\,BK_\alpha}{}^A$ being designated $\alpha_{CF\,BK_\alpha}{}^A$;

(B) positioning a sample comprising said substrate with said layers thereon in said system for measurement;

(C) measuring the number of counts in the $AL_\alpha$, $BK_\alpha$ and $CK_\alpha$ line windows of said sample in response to x-ray excitation;

(D) calculating the initially assumed thickness $t_{AF}$ of the A layer of said sample in accordance with the following relationship:

$$t_{AF} = \frac{1}{\alpha_6} \ln\left(1 - \frac{AL_\alpha}{AL_{\alpha\infty}}\right)^{-1}$$

where $AL_\alpha$ is the measured count in the $AL_\alpha$ line window;

(E) calculating the thickness $t_B$ of the B layer of said sample in accordance with the following relationship:

$$t_B = \frac{1}{\alpha_3} \ln\left(1 - \frac{BK_\alpha}{BK_{\alpha\infty}} e^{\alpha^A_{CF_{BK_\alpha}} t_{AF}}\right)^{-1}$$

where $BK_\alpha$ is the measured count in the $BK_\alpha$ line window;

(F) calculating the thickness $t_A$ of the A layer of said sample in accordance with the following relationship:

$$t_A = \frac{1}{\alpha^A_{CK_\alpha}} \ln\left(\frac{CK_{\alpha\infty} e^{-\alpha^B_{CK_\alpha} t_B}}{CK_\alpha - \alpha_5 BK_\alpha(1 + (\alpha_{CF_{BK_\alpha}}^A - \alpha^A_{CK_\alpha}) t_{AF})}\right)$$

where $CK_\alpha$ is the measured count in the $CK_\alpha$ line window;

(G) and, if $t_A$ calculated in step (F) differs from $t_{AF}$ by more than a prescribed amount, successively iterating steps (E) and (F) while using for $t_{AF}$ the value just previously calculated for $t_A$ in step (F).

7. A method as in claim 6 wherein said metals A, B and C comprise gold (Au), nickel (Ni) and copper (Cu), respectively, and wherein step C comprises measuring the number of counts in the $AuL_\alpha$, $NiK_\alpha$ and $CuK_\alpha$ line windows of said sample in response to x-ray excitation.

8. In combination in an x-ray-fluorescence system for measuring the thicknesses of the thin-film components of a sample that comprises thin films deposited on top of each other on a substrate, means for irradiating said sample with incident x-rays to excite x-ray-fluorescence in said films and substrate, and means for detecting the x-ray-fluorescence emitted by said sample, wherein the improvement comprises a collimator assembly interposed between said sample and said detector means to maximize the collection of flux from said sample, said assembly comprising an x-ray-absorptive housing havng a conically shaped bore whose relatively small end is designed to be positioned immediately adjacent a surface of said sample to be measured.

9. In combination in an x-ray-fluorescence system for measuring the thicknesses of the thin-film components of a sample that comprises thin films deposited on top of each other on a substrate, means for irradiating said sample with incident x-rays to excite x-ray-fluorescence in said films and substrate, and means for detecting the x-ray-fluorescence emitted by said sample, wherein the improvement comprises a collimator assembly interposed between said sample and said detecting means, said assembly comprising a lead housing having at least one flat surface and having a single conically shaped bore whose relatively small end is immediately adjacent said flat surface so that a sample mounted on said flat surface can be located immediately adjacent the small end of said bore, and means responsive to a portion of said incident x-rays for supplying to said detecting means a characteristic line count representative of the output intensity of said irradiating means, wherein said supplying means comprises an opening in the side of said housing to allow passage therethrough and into the bore of said collimator assembly of some of said incident x-rays to excite x-ray-fluorescence of said lead within said bore, whereby the fluorescence of said lead is monitored by said detecting means to provide a measure of the intensity of said incident x-rays.

10. A method for measuring the thickness of the gold film included in a sample that comprises a gold film on a copper substrate, said method comprising the steps of
irradiating such a sample with x-rays to excite fluorescence in said sample,
measuring the respective number of counts in the $AuL_\alpha$ and $AuM_\alpha$ line windows of said sample in response to said irradiation,
and calculating the ratio of the $AuL_\alpha$ count to the $AuM_\alpha$ count to obtain a measure of the thickness of said gold film.

* * * * *